United States Patent [19]

Koller

[11] Patent Number: 4,631,072
[45] Date of Patent: Dec. 23, 1986

[54] MIXTURE FOR THE CARE AND CLEANING OF CONTACT LENSES

[76] Inventor: Anton Koller, Operngasse 23, 1040 Wien, Austria

[21] Appl. No.: 806,975

[22] Filed: Dec. 9, 1985

[30] Foreign Application Priority Data

Dec. 10, 1984 [AT] Austria ............................ 3910/84

[51] Int. Cl.$^4$ .......................... B24D 3/06; C09C 1/04
[52] U.S. Cl. ........................................ 51/309; 51/308
[58] Field of Search ...................... 51/309, 308; 134/7

[56] References Cited

U.S. PATENT DOCUMENTS

| | | | |
|---|---|---|---|
| 4,021,263 | 5/1977 | Rosenblum | 51/309 |
| 4,126,899 | 7/1979 | Molnar et al. | 51/309 |
| 4,242,842 | 1/1981 | Yancey | 51/309 |
| 4,358,295 | 11/1982 | Namba et al. | 51/309 |
| 4,389,819 | 6/1983 | Williamson et al. | 51/309 |
| 4,394,179 | 6/1983 | Ellis et al. | 134/7 |
| 4,529,410 | 7/1985 | Khaladji et al. | 51/309 |

FOREIGN PATENT DOCUMENTS

3021034 1/1981 Fed. Rep. of Germany .
2108699 5/1983 United Kingdom .

*Primary Examiner*—Prince E. Willis
*Assistant Examiner*—Willie J. Thompson
*Attorney, Agent, or Firm*—Young & Thompson

[57] ABSTRACT

The disclosure relates to a mixture for the care and cleaning of contact lenses, containing water, an abrasive based on one or several metal oxides, and a suspension aid based on swellable compounds. The abrasive is zinc oxide and/or tin oxide having a grain size smaller than 10 $\mu$m and a suspension aid based on swellable compounds, such as polyvinyl alcohol, cellulose derivatives, guar gum, as well as optionally buffers for adjusting the pH value to between 5 and 8 and/or sodium chloride, the ratio of abrasive to water in the mixture ranging between 1:99 and 90:10, and the grain size of the abrasive being preferably in a range of 0.5 $\mu$m.

8 Claims, No Drawings

MIXTURE FOR THE CARE AND CLEANING OF CONTACT LENSES

The invention relates to a mixture for the care and cleaning of contact lenses, containing water, an abrasive based on one or several metal oxides having a grain size smaller than 10 μm and a suspension aid based on swellable compounds, such as polyvinyl alcohol, cellulose derivatives, guar gum, as well as optionally buffers for adjusting the pH value to between 5 and 8 and/or sodium chloride, the ratio of abrasive to water in the mixture ranging between 1:99 to 90:10.

Contact lenses are understood to mean visual aids consisting, for example, of polyhydroxyethylmethacrylate crosslinked with ethylene glycol methacrylate, or siloxane compounds or also protein compounds.

Hard contact lenses absorb hardly any water at all, as is the case with the hydrophilic, soft contact lenses; consequently, the use of conventional, aggressive cleaning agents and disinfectants after wearing hard contact lenses causes virtually no problems. However, it has been observed that hard contact lens care agents containing benzalkonium chloride or chlorobutanol give rise to hydrophobic lens surfaces and, in particular, are incompatible with several siloxane-containing lens materials.

It is furthermore known that the cleaning and caring agents usable for hard contact lenses must not be employed with soft contact lenses since various active agents contained in the cleaning and/or care agent accumulate in the lens material. The consequence is an irreversible damage to the lens material as well as possibly serious injury to the eye.

It is an irrefutable fact, however, that it is necessary to clean contact lenses, and thus this also holds true for soft contact lenses. The contact lenses float on a film of tears consisting of a mucous layer covering the cornea, the actual tears constituting an aqueous phase, and a thin, oily film. The mucous layer serves the purpose of rendering the cornea hydrophilic and hygroscopic, whereas the oily film is to retard the evaporation of the film of tears. The mucous layer consists primarily of proteins secreted by the various glands in the eyelids. When removing the contact lens from the eye, protein residues will adhere to the lens which will subsequently become denatured and can then be removed only with difficulties. These protein residues are also a suitable nutrient substrate for germs (bacteria) so that it is necessary to regularly free the contact lenses of these germs and undesirable residues.

Cleaning contact lenses by purely chemical methods is practically impossible because of the protein residues which adhere to the surface of the lenses and may be more or less denatured.

Therefore, the purely chemical cleaning agents, that have been suggested in various instances and operate, in part, also with hydrogen peroxide split under the effect of a catalyst (cf. European Laid-Open Application 0 082 798 or U.S. Pat. No. 4,396,583), are inadequate.

It has also been proposed, therefore (cf. U.S. Pat. No. 4,394,179 or DOS 3,021,034), to suspend in cleaning solutions, besides a surface-active agent, an abrasive based on metallic oxides, together with a suspension aid, in an aqueous solution or an organic fluid. U.S. Pat. No. 4,394,179 suggests particle sizes of up to 10 μm, in this context. A disadvantage in the cleaning and care agent for contact lenses known from U.S. Pat. No. 4,394,179 is the circumstance that this agent must in any event contain a surfactant and that it is suited primarily only for the cleansing of hard contact lenses.

The invention is based on the object of providing, starting with the state of the art defined by U.S. Pat. No. 4,394,179, a mixture for the cleaning and care of contact lenses that can be used without problems not only for hard contact lenses but also for soft contact lenses.

This object has been attained according to the invention in that the abrasive is zinc oxide and/or tin oxide. The grain size of the abrasive is preferably in the range of 0.5 μm.

Furthermore, the provision can be made within the scope of this invention that the mixture contains sodium chloride in an amount at which the osmotic pressure of the mixture is essentially the same as the osmotic pressure of tear fluid.

The mixture of this invention does not contain any active ingredients penetrating into the material of soft contact lenses, which can accumulate therein and can subsequently cause damage to the eye. Another advantage of the mixture of this invention resides in that, in the use of the mixture of this invention for cleaning purposes (rubbing the lens surface between the pads of one's fingers), no traces of abrasion are caused in the material of the contact lens that are deeper than they are present anyway in the surfaces of the contact lenses due to their manufacture. The metal oxides suggested by the invention as abrasive media, namely zinc oxide and/or tin oxide, are materials exhibiting an only relatively low internal hardness so that the lens surface, when friction is applied while using the mixture of this invention, will neither be damaged nor altered. An essential feature of the mixture of this invention resides in that the abrasive is present in a uniform grain size which is smaller than 10 μm and ranges preferably on the order of magnitude of 0.5 μm.

The suspension of the abrasive particles in the water is stabilized by the suspension aids, such as, for example, hydroxyethylcellulose, xanthan gum, guar gum, polyvinyl alcohol, methylcellulose, or other conventional extenders.

By adding a buffering agent and/or by the admixture of sodium chloride to the emulsion, the latter is extensively adapted to tear fluid with respect to the pH value and the osmotic pressure.

The use of zinc oxide as the abrasive, preferred according to this invention, additionally affords the advantage that the zinc ions bring about a partial saponification of the residues on the contact lens surface, on account of the minor alkaline activity of the ions, and thus a weak surface-active effect results even without the addition of surfactants.

On account of the fact that, for example by the addition of sodium chloride, the mixture of this invention is brought close to the properties of a physiological sodium chloride solution with respect to its osmotic pressure, it is ensured that the contact lens cannot affix itself to the eye even in case of improper usage, i.e. in case the zinc emulsion of this invention has not been flushed away from the contact lens with adequate care.

The metallic oxides contained in the mixture of this invention (zinc oxide and/or tin oxide), with the use of a mixture ratio of 1:99 (agent similar to a solution) to 90:10 (pasty emulsified product) are kept in suspension in dependence on the viscosity desired by means of one or several of the above-mentioned extenders. After cleansing hard and especially soft contact lenses by rubbing same with the use of the mixture according to this invention, the contact lenses can be freed of adhering mixture residues by the use of physiological sodium chloride solution or another rinsing agent. Subsequently, the contact lens can be put away overnight, as usual.

It is possible, when using the agent of this invention, also to refrain from rinsing the contact lens after rubbing and use of the mixture of this invention, and, rather, store the contact lens directly overnight. This procedure has the advantage that the above-described saponification effect acts overnight and in some cases even longer and in such a case it is sufficient to rinse away, shortly prior to use, the residue together with the impurities with the aid of an appropriate rinsing solution.

Of course, it is also possible to combine the use of the mixture according to this invention for the care and cleaning of contact lenses with a conventional cleaning agent, for example one based on hydrogen peroxide. For this purpose, the contact lens rubbed with the mixture of this invention can be placed for some time, for example for 15 minutes up to 8 hours, into a hydrogen peroxide solution having a concentration of 0.5% to 30%. By the catalytic action of the zinc oxide or tin oxide contained in the agent of this invention, the hydrogen peroxide is cleaved into water and oxygen so that additionally sterilization of the contact lens is achieved.

It has been found that the mixture of this invention is not only suitable for caring for soft or hard contact lenses, but also for the cleansing of highly gas-permeable, hard contact lenses, such as, for example, those made of materials exhibiting a high siloxane proportion for obtaining high gas permeability. Included herein are, for example, the materials "Boston II" and "Boston IV" by the company Polymer Technologies (Wilmington, Mass., USA) or "Paraperm" or "Paraperm EW" by the company Paragon (Mesa, Ariz., USA), these materials being most fluorosilicone methacrylates.

However, in order to achieve additional cleansing action, the mixture of this invention can be combined with a nonionic surfactant, such as, for example, "Tego Betain HS" (an ampholytic surfactant based on betaine by the company Th. Goldschmidt). Thereby an improved wetting of the contact lens surface is likewise brought about.

An example for the combined utilization of hydrogen peroxide and the mixture of this invention will be set forth below:

Practical Example:

The contact lens is placed for 10 minutes to 12 hours into a hydrogen peroxide solution of 0.5–30% strength, then rinsed off with 0.9% strength isotonic sodium chloride solution and stored in likewise 0.9% strength isotonic sodium chloride solution. Thereupon 1 ml to 10 ml of the mixture of this invention (emulsion) is added thereto, and the contact lens is left therein for one hour to 12 hours. In order to improve the cleansing effect, it is recommended to slightly rub the contact lens between the pads of one's fingers at least once after adding the mixture of this invention in order to enhance the cleaning effect.

After storage is finished, the cleaned and sterilized contact lens is rinsed with 0.9% strength sodium chloride solution and can be utilized immediately.

Several examples for mixtures of this invention, containing tin oxide or the preferred zinc oxide, are set out below.

EXAMPLE 1

1 l of distilled water
9 g of sodium chloride
73 g of zinc oxide
2.82 g of "Natrosol" (nonionic hydroxyethylcellulose; manufacturer: Fa. Hercules in Rijswijk, Netherlands)

EXAMPLE 2

1 l of distilled water
1.5 g of xanthan gum (a polysaccharide produced by the fermentation method)
8 g of sodium chloride
97 g of zinc oxide

EXAMPLE 3

10% by weight of zinc oxide
20% by weight of nonionic surfactant (e.g. "Tego Betain HS")
1.5% by weight of guar gum
68.5% by weight of distilled water

EXAMPLE 4

15% by weight of zinc oxide
15% by weight of nonionic surfactant (e.g. "Tego Betain HS")
5% by weight of "Natrosol"
65% by weight of physiological sodium chloride solution The thickener, e.g. xanthan gum, exhibits an unpleasant odor, when dissolved in water, and for this reason it is possible to provide improvement of the scent by adding small amounts of fragrances, such as, for example, lime oil, peppermint or rosemary oil.

It is possible within the scope of this invention to utilize other surfactants which are detergent materials.

What is claimed is:

1. Mixture for the care and cleaning of contact lenses, containing water, an abrasive which is at least one metal oxide having a grain size smaller than 10 $\mu$m, and a suspension aid, the ratio of abrasive to water in the mixture ranging between 1:99 and 90:10, the abrasive being at least one member selected from the group consisting of zinc oxide and tin oxide.

2. Mixture according to claim 1, which contains sodium chloride in an amount at which the osmotic pressure of the mixture is essentially the same as the osmotic pressure of human tears.

3. Mixture according to claim 1, in which the grain size of the abrasive is substantially uniform and is about 0.5 $\mu$m.

4. Mixture according to claim 1, which contains a surfactant in a substantial amount up to 25% by weight, based on the total weight of the mixture.

5. Mixture according to claim 1, in which said suspension aid is at least one member selected from the group consisting of hydroxyethylcellulose, xantham gum, guar gum, polyvinyl alcohol, and methylcellulose.

6. Mixture according to claim 1, in which said member is zinc oxide.

7. Mixture according to claim 1, containing also a buffering agent for adjusting the pH value to between 5 and 8.

8. Mixture according to claim 1, in the form of an emulsion.

* * * * *